(12) United States Patent
Chen et al.

(10) Patent No.: US 11,471,033 B2
(45) Date of Patent: Oct. 18, 2022

(54) CAPSULE CORE AND CAPSULE ENDOSCOPE

(71) Applicant: ANKON TECHNOLOGIES CO., LTD, Wuhan (CN)

(72) Inventors: Yun Chen, Wuhan (CN); Nianqi Zhou, Wuhan (CN); Yunwen Chen, Wuhan (CN)

(73) Assignee: ANKON TECHNOLOGIES CO., LTD., Wuhan (CN)

( * ) Notice: Subject to any disclaimer, the term of this patent is extended or adjusted under 35 U.S.C. 154(b) by 124 days.

(21) Appl. No.: 17/029,969

(22) Filed: Sep. 23, 2020

(65) Prior Publication Data

US 2021/0085163 A1    Mar. 25, 2021

(30) Foreign Application Priority Data

Sep. 23, 2019    (CN) .......................... 201910899452.0

(51) Int. Cl.
| | |
|---|---|
| *H01R 12/00* | (2006.01) |
| *H05K 1/00* | (2006.01) |
| *A61B 1/04* | (2006.01) |
| *A61B 1/00* | (2006.01) |
| *A61B 1/06* | (2006.01) |
| *H05K 1/14* | (2006.01) |

(52) U.S. Cl.
CPC ............ *A61B 1/041* (2013.01); *A61B 1/0011* (2013.01); *A61B 1/00016* (2013.01); *A61B 1/00032* (2013.01); *A61B 1/00158* (2013.01); *A61B 1/0661* (2013.01); *H05K 1/144* (2013.01); *H05K 1/147* (2013.01); *H05K 2201/10037* (2013.01); *H05K 2201/10098* (2013.01); *H05K 2201/10121* (2013.01)

(58) Field of Classification Search
CPC . A61B 1/041; A61B 1/00016; A61B 1/00032; A61B 1/0011; A61B 1/00158; A61B 1/0661; H05K 1/144; H05K 1/147; H05K 2201/10037; H05K 2201/10098; H05K 2201/10121
USPC .......................................................... 439/66
See application file for complete search history.

(56) References Cited

U.S. PATENT DOCUMENTS

2007/0142704 A1 * 6/2007 Wu ........................ A61B 1/041
600/109

FOREIGN PATENT DOCUMENTS

WO    WO-2019190057 A1 * 10/2019 ......... A61B 1/00016

* cited by examiner

*Primary Examiner* — Andargie M Aychillhum
(74) *Attorney, Agent, or Firm* — Treasure IP Group, LLC

(57) ABSTRACT

A capsule core and a capsule endoscope are provided. The capsule core includes a printed circuit board module, connecting structures and functional units. The printed circuit board module includes more than more printed circuit boards connected through flexible circuit boards and spaced apart. The connecting structures connect adjacent printed circuit boards. The functional units are mounted on the printed circuit boards or the connecting structures, and at least part of the functional units communicates with the printed circuit boards.

9 Claims, 8 Drawing Sheets

CAPSULE CORE AND CAPSULE ENDOSCOPE

CROSS-REFERENCE OF RELATED APPLICATIONS

The application claims priority to Chinese Patent Application No. 201910899452.0 filed on Sep. 23, 2019, the contents of which are incorporated by reference herein.

FIELD OF INVENTION

The present invention relates to the art of capsule device for use in medical related applications, and more particularly to an integrated capsule core and a capsule endoscope with the capsule core.

BACKGROUND

Nowadays, capsule endoscope can be effectively used in the diagnosis of gastrointestinal diseases due to its advantages of convenient examination, with no invasion and pain, and not affecting the normal life of patients.

Usually, the capsule endoscope comprises an enclosure and a capsule core built in the enclosure. The capsule core is the core structure of the capsule endoscope, which comprises but is not limited to a plurality of functional components, such as a photographing unit and a signal transmission unit. Of the existing capsule endoscope, the internal components are scattered and fixed in the core structure, and the core structure is relatively unstable, which causes inconvenient fixing.

SUMMARY OF THE INVENTION

The present invention discloses an integrated capsule core and a capsule endoscope with the capsule core.

It is one object of the present invention to provide a capsule core, comprising:

a printed circuit board module, comprising a plurality of printed circuit boards connected through flexible circuit boards and spaced apart; a plurality of connecting structures for connecting adjacent printed circuit boards; and a plurality of functional units that are mounted on the printed circuit boards or the connecting structures, at least part of the functional units communicating with the printed circuit boards.

It is another object of the present invention to provide a capsule endoscope, comprising:

an enclosure and the capsule core as described above.

The capsule core disclosed in the patent application connects adjacent printed circuit boards through connecting structures, and the functional units are mounted on the printed circuit boards or the connecting structures. Therefore, the capsule core forms a whole structure, which is convenient for fixing to the enclosure.

DETAILED DESCRIPTION

The present invention can be described in detail below with reference to the accompanying drawings and preferred embodiments. However, the embodiments are not intended to limit the invention, and the structural, method, or functional changes made by those skilled in the art in accordance with the embodiments are comprised in the scope of the present invention.

In the figures of the present invention, some sizes of a structure or portion may be exaggerated relative to other structures or portions for ease of illustration, and thus, are merely used to illustrate the basic structure of the subject matter of the present invention.

In the present invention, for the convenience of description, the inside of the enclosure of the capsule endoscope is described as inner side, and the outside of the enclosure is described as outer side.

Figure 1:
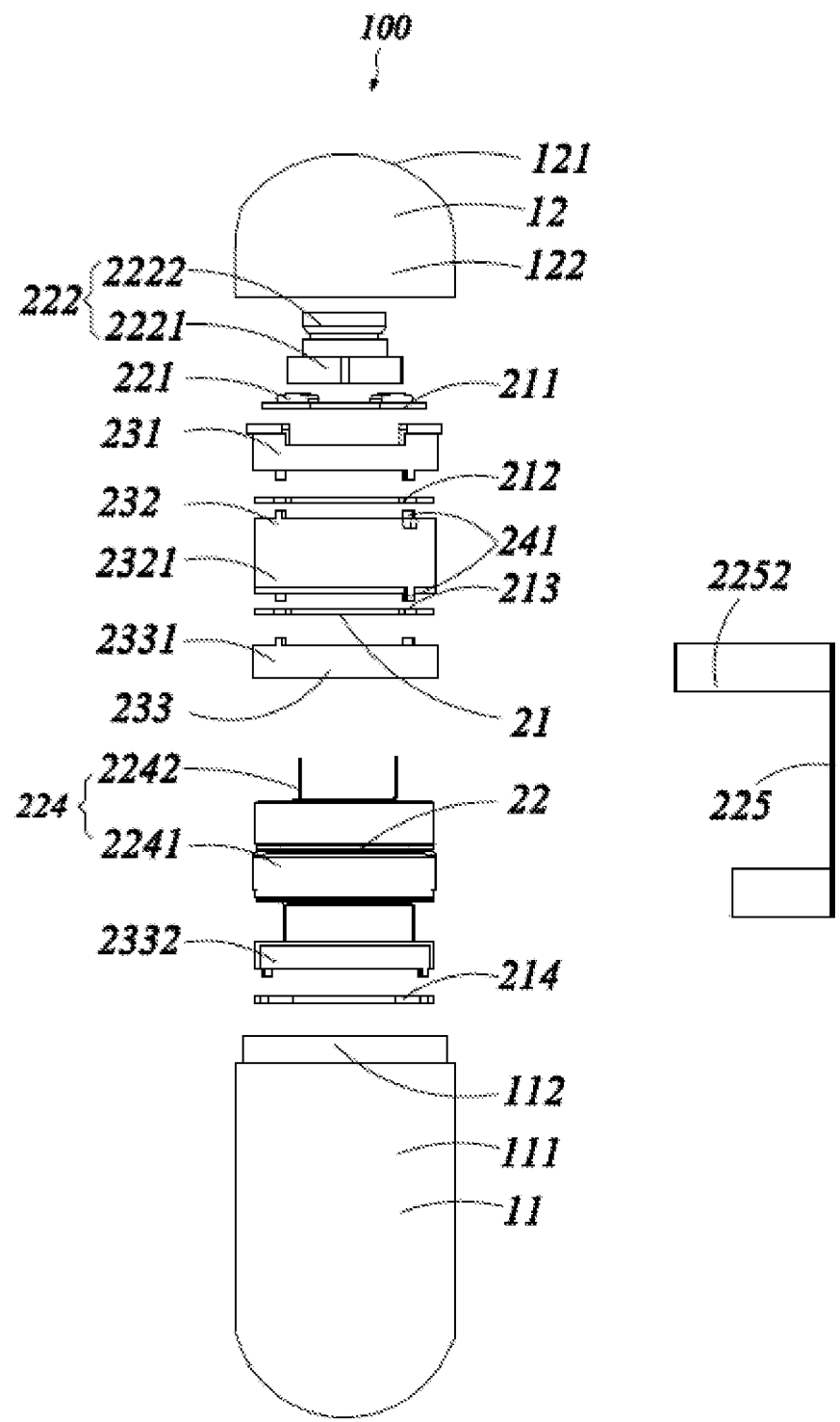
FIG. 1 is an exploded schematic diagram of a capsule endoscope according to a preferred embodiment of the present invention.
Figure 2:
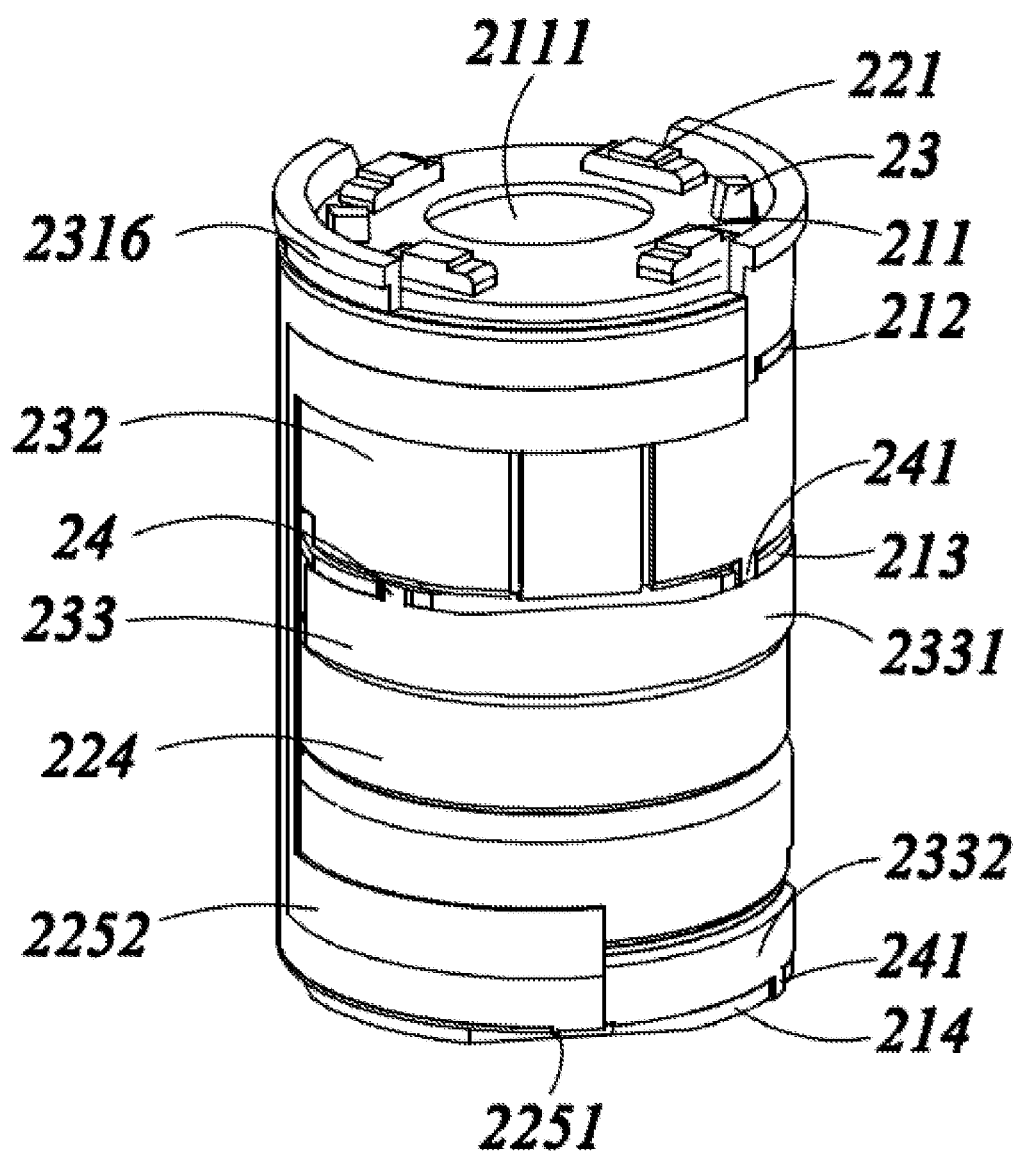
FIG. 2 is a schematic diagram of the structure of a capsule core which does not comprise a photographing unit according to the embodiment shown in FIG. 1.
Figure 3:
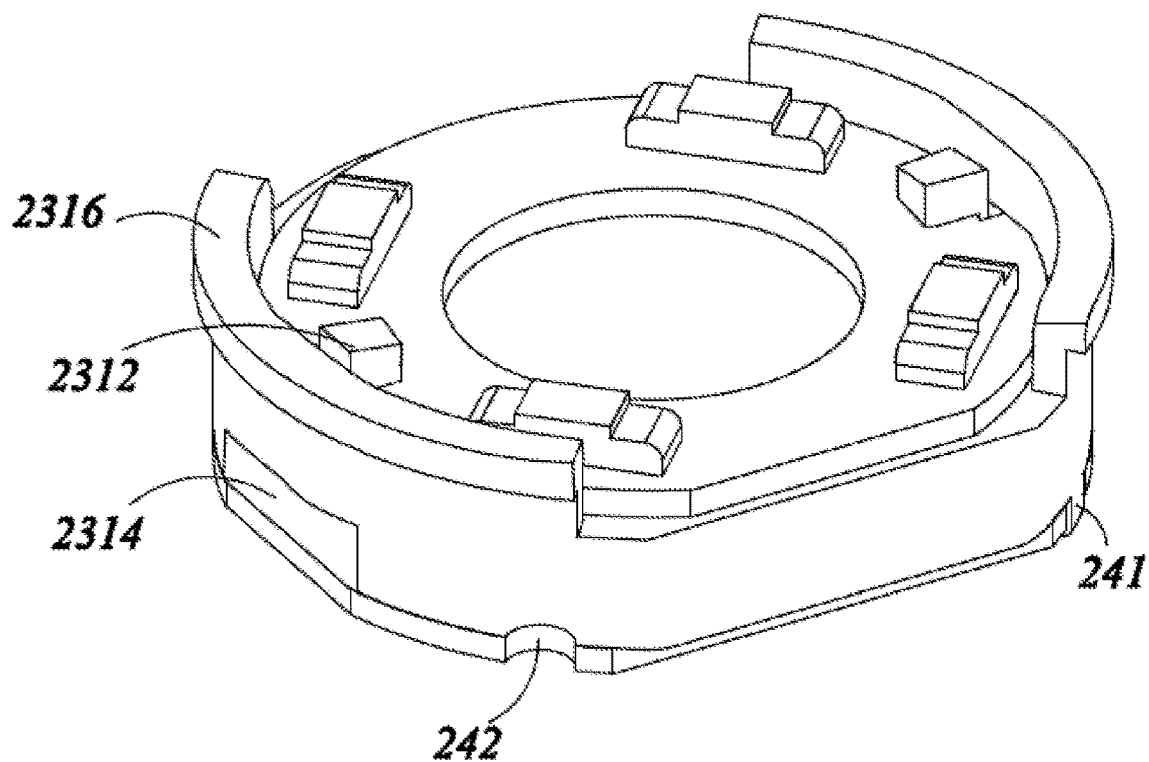
FIG. 3 is a schematic diagram of a first PCB, a second PCB and a first connector which are fixed together according to the embodiment shown in FIG. 1.
Figure 4:
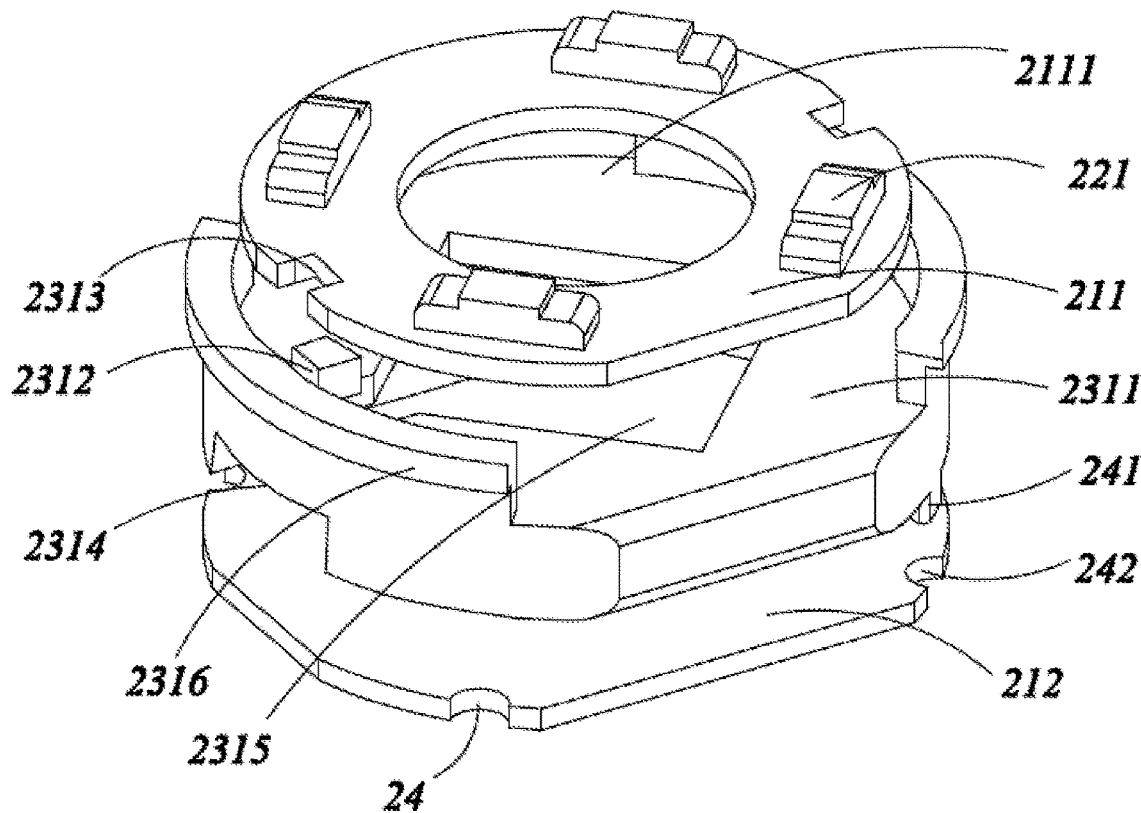
FIG. 4 is an exploded schematic diagram of FIG. 3.
Figure 5:
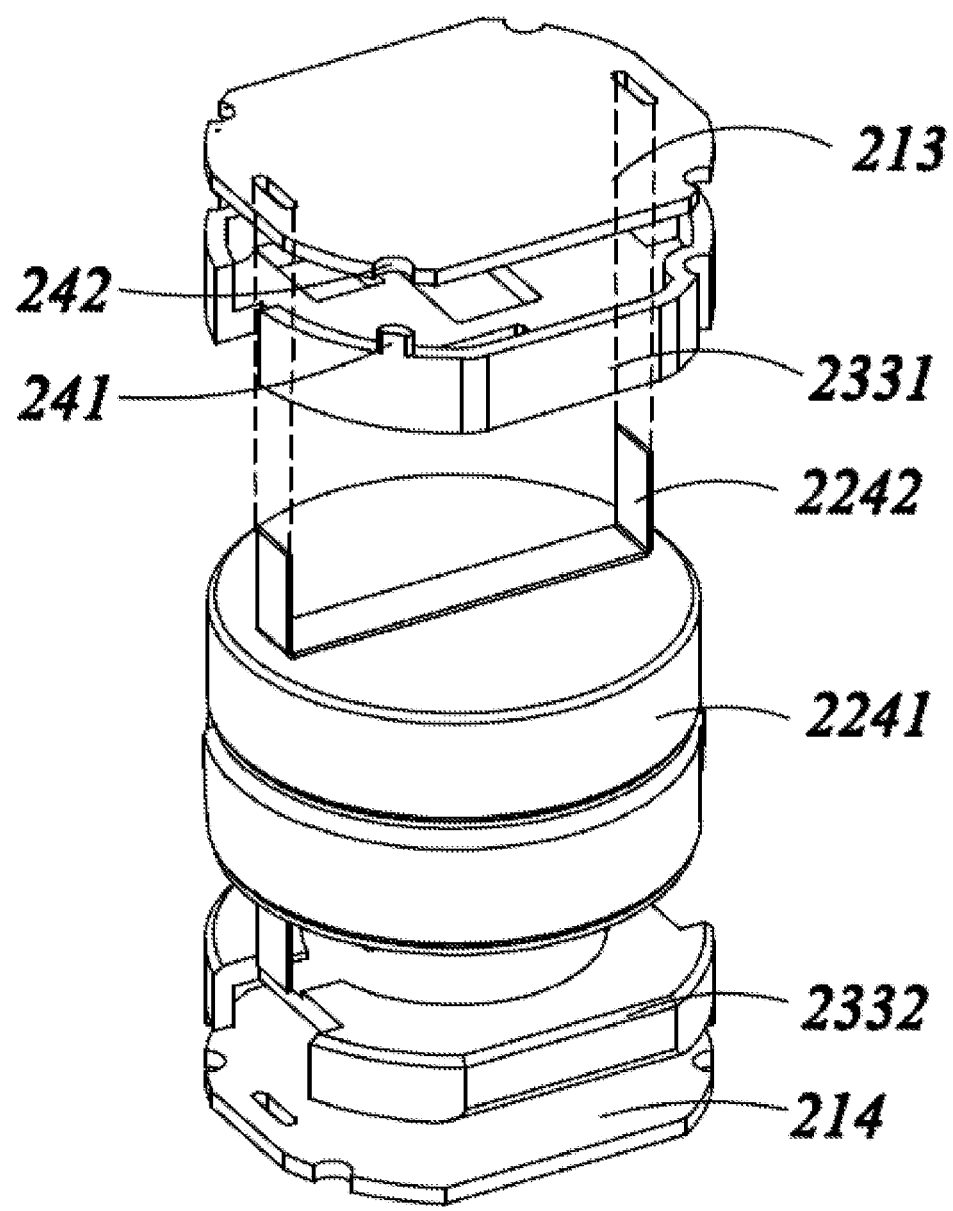
FIG. 5 is a schematic diagram of a battery unit, an adjacent third PCB and an adjacent fourth PCB which are not assembled according to the embodiment shown in FIG. 1.
Figure 6:
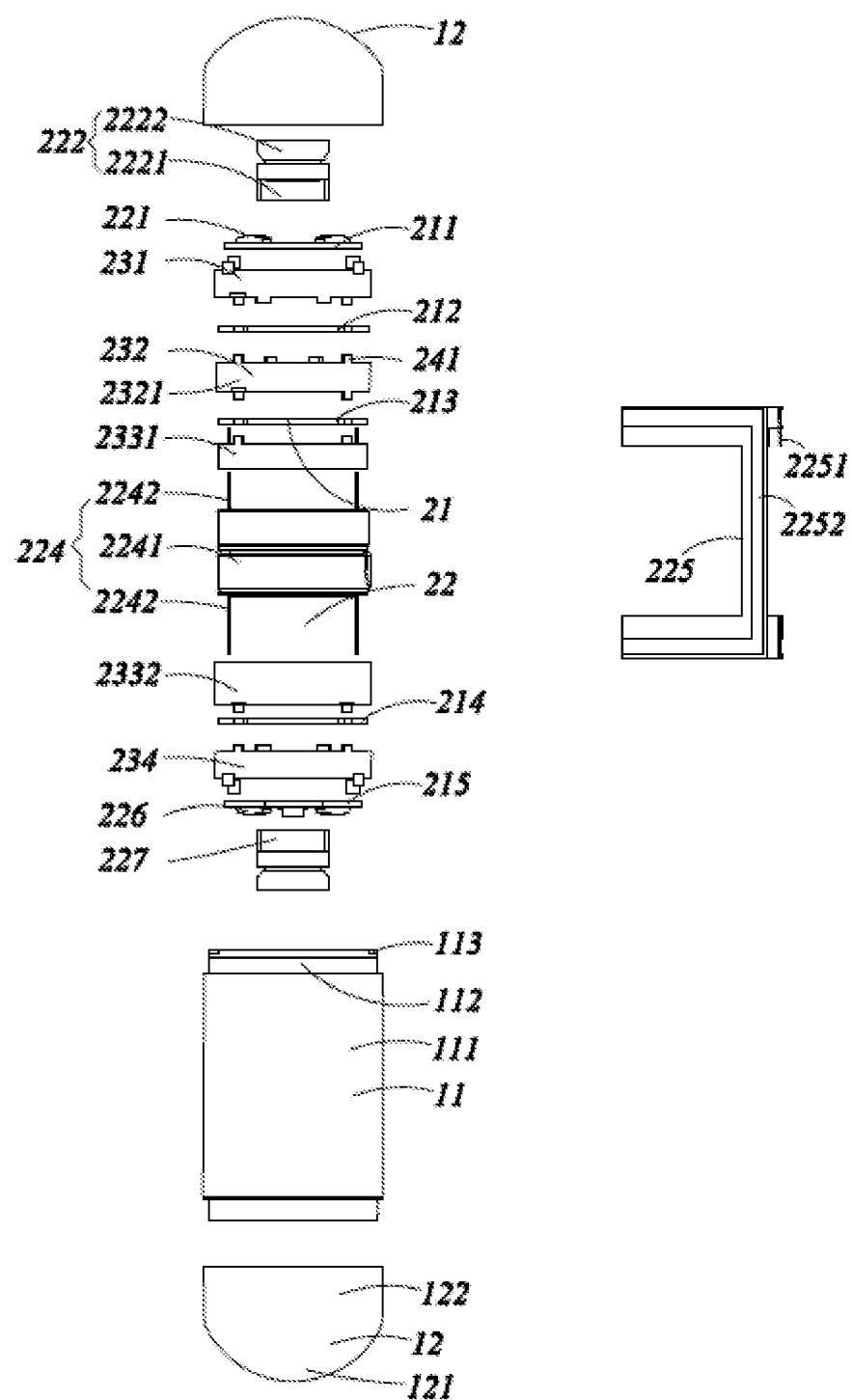
FIG. 6 is an exploded schematic diagram of the capsule endoscope according to another embodiment of the present invention.
Figure 7:
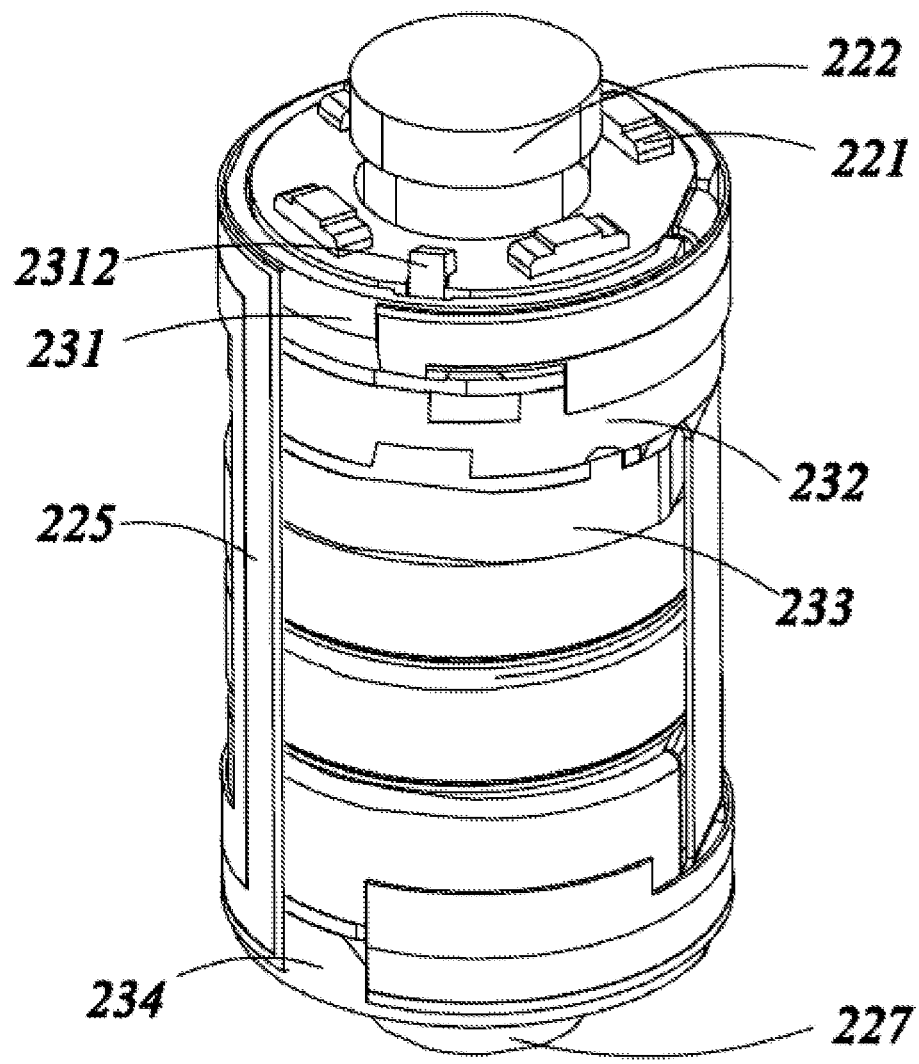
FIG. 7 is a schematic diagram of the structure of an entire capsule core according to the embodiment shown in FIG. 6.
Figure 8:
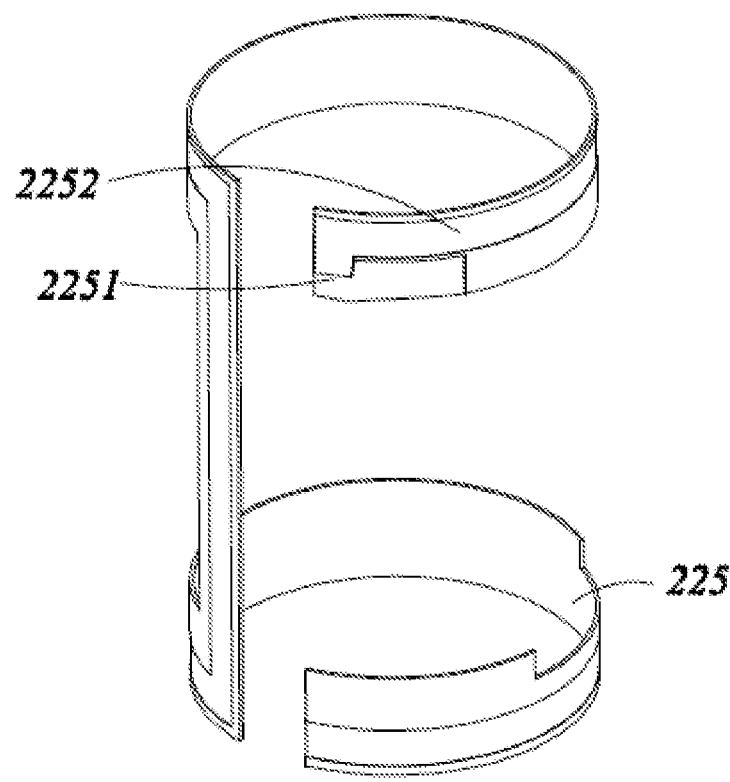
FIG. 8 is a schematic diagram of the structure of an antenna according to the embodiment shown in FIG. 6.
Figure 9:
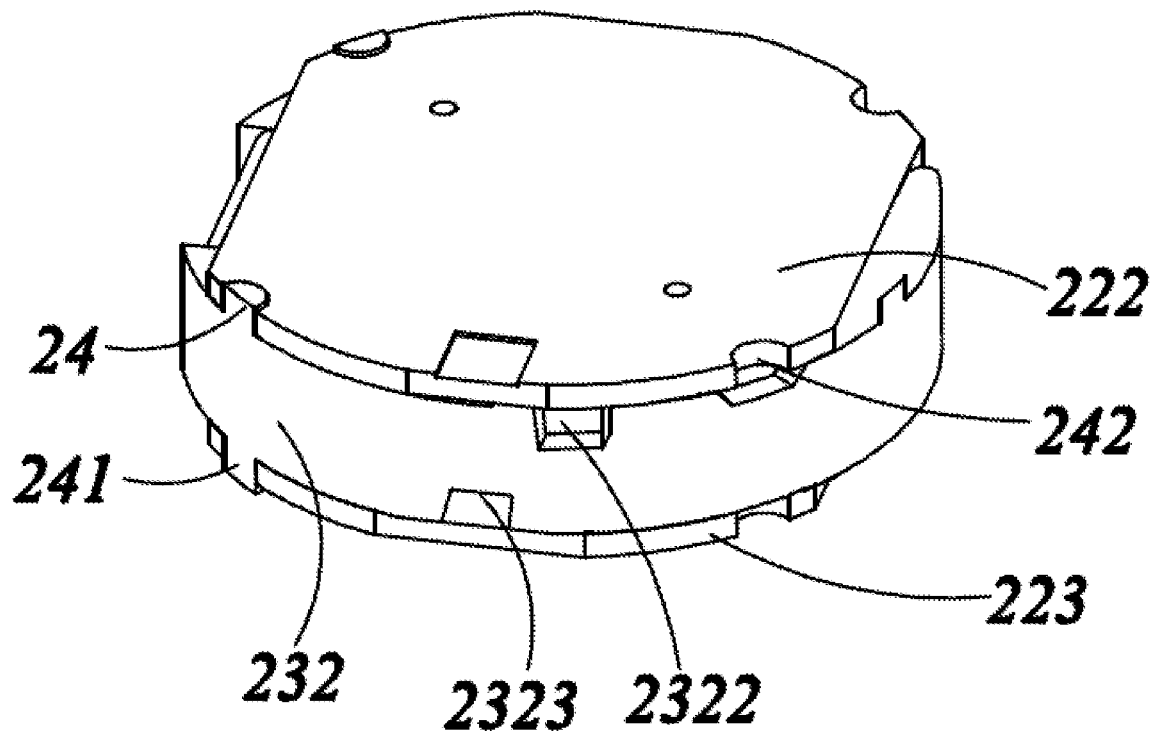
FIG. 9 is a schematic diagram of the structure of a second PCB, an electromagnetic unit and a third PCB according to the embodiment shown in FIG. 6.
Figure 10:
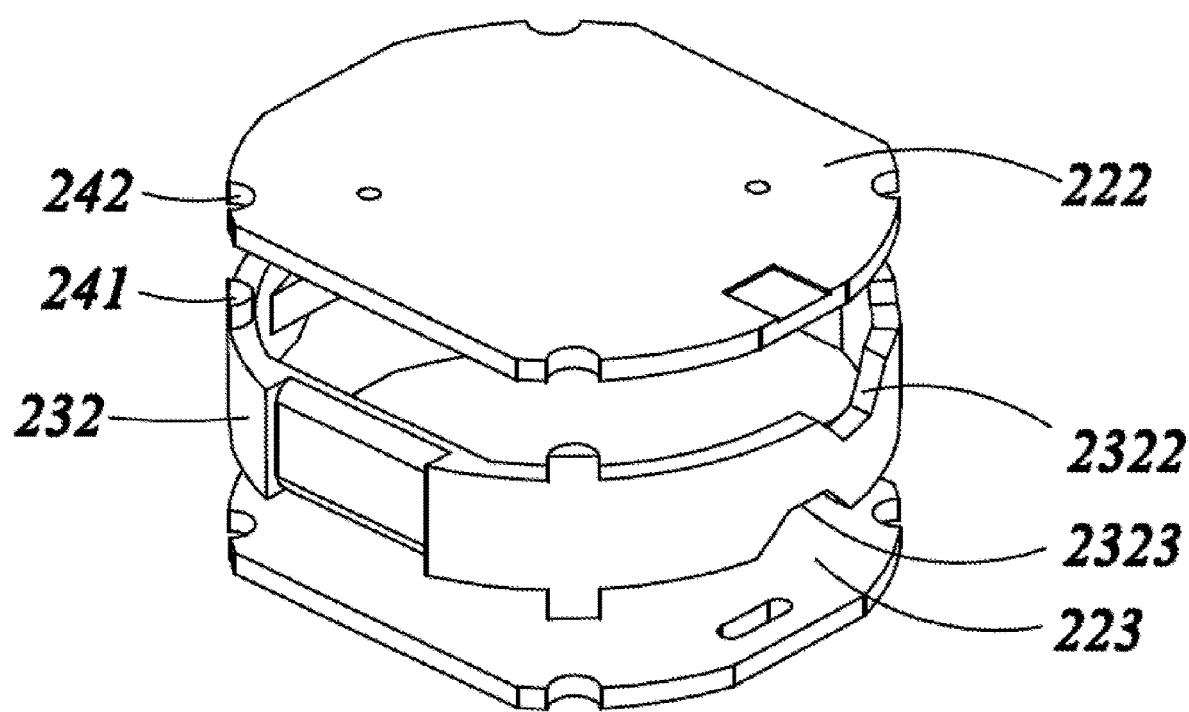
FIG. 10 is an exploded schematic diagram of FIG. 9.

Referring to FIGS. 1-10, showing a preferred embodiment of a capsule endoscope 100 according to the present invention.

The capsule endoscope 100 comprises an enclosure 1 and a capsule core 2 built in the enclosure 1, wherein the capsule core 2 is fixed in the enclosure 1.

The enclosure 1 is biocompatible and cannot be corroded by digestive fluid. It can be made still using the material of the enclosure 1 in the existing capsule endoscope 100, or designed separately.

The enclosure 1 comprises at least two parts joined together to facilitate fixing the capsule core 2 in the enclosure 1. For example, as shown in FIGS. 1-5, the enclosure 1 comprises a main enclosure 11 and a transparent end cover 12 disposed at one end of the main enclosure 11, which is suitable for a single-camera capsule endoscope 100. Wherein, the transparent end cover 12 and the main enclosure 11 are joined along the axial direction of the capsule endoscope 100 to form the enclosure 1, and the two are connected to each other by screwing, gluing, clamping or other methods. Preferably, gluing is used for good sealing.

Alternatively, as shown in FIGS. 6-10, the enclosure 1 comprises a main enclosure 11 with both ends open, and two transparent end covers 12 respectively disposed at both ends of the main enclosure 11, which is suitable for a dual-camera capsule endoscope 100. The transparent end covers 12 and the main enclosure 11 are connected in the same way as described above, and cannot be further described.

Further, the end cover 12 comprises a transparent cover body 121, and a first connecting portion 122 protruding from the outer half of the transparent cover body 121 toward the main enclosure 11. The "outer half" refers to a portion projecting inward from the outer wall and not reaching the inner wall, and a step is formed between the first connecting portion 122 and the transparent cover body 121.

The main enclosure 11 comprises a main enclosure body 111, and a second connecting portion 112 protruding from the inner half of the main enclosure body 111 toward the end cover 12. The "inner half" refers to the portion projecting outward from the inner wall and not reaching the outer wall, and a step is formed between the second connecting portion 112 and the main enclosure body 111.

The first connecting portion 122 is fitted over the second connecting portion 112 to realize the connection between the end cover 12 and the main enclosure 11. The enclosure 1 further comprises a glue-accommodating groove located between the first connecting portion 122 and the second connecting portion 112 for accommodating the glue for bonding the end cover 12 and the main enclosure 11, and for good sealing performance. Those skilled in the art can understand that the glue accommodating groove is provided in at least one of the inner wall of the first connecting portion 122 and the outer wall of the second connecting portion 112.

In addition, the second connecting portion 112 is shorter than the first connecting portion 122, and the transparent cover body 121, the first connecting portion 122 and the second connecting portion 112 jointly form a fixing groove (not shown) for fixing the capsule core 2. Or, an end of the main enclosure 11 has a snap-fit protrusion 113 protruding inward, which is convenient for fixing the capsule core 2. Specifically, after assembly, this component enables the capsule core 2 to be securely fixed to the enclosure 1, and during the motion of the capsule transparent, it ensures that the position of the photographing unit relative to the transparent cover body remains unchanged, so that the image quality is improved.

Different from the above embodiment, the connections of the enclosure 1 can also be designed such that the first connecting portion protrudes from the inner half of the transparent cover toward the main enclosure, and the second connecting portion protrudes from the outer half of the main enclosure toward the end cover, wherein the first connecting portion and the second connecting portion are joined over each other, and the main enclosure, the second connecting portion and the first connecting portion jointly form the fixing groove.

In the present application, the capsule core 2 has an integral structure, which is convenient for integral assembly with the enclosure 1.

The capsule core 2 comprises a printed circuit board (PCB) module 21, a plurality of connecting structures 23 that connect adjacent PCBs, and a plurality of functional units 22 which are fixed on the PCBs or the connecting structures 23. It can also be understood that the connecting structures 23 connect the PCB module 21 and the functional units 22 as a whole.

The PCB module 21 comprises a plurality of PCBs connected through flexible printed circuit boards and spaced apart, and the number of the PCBs is determined based on the number and type of the functional units 22. By bending the flexible circuit boards, the PCBs are arranged in parallel, and the functional units 22 can be placed between adjacent PCBs. The parallel arrangement in this application refers to a substantially parallel arrangement, not specifically to a strict parallel arrangement in a geometric sense.

The functional units 22 are core components of the capsule core 2, and at least part of the functional elements of the functional units 22 communicate with the PCBs. Those skilled in the art can understand that not all the functional units 22 need to be connected to the PCBs, that is, the functional elements of the functional unit 22 such as photographing unit and antenna unit that need to communicate with the PCBs are connected to the PCBs for communication, but other functional units 22, such as the magnet unit 223, only need to be mechanically connected to the adjacent PCBs.

The connecting structures 23 connect adjacent PCB, and the structure and connection mode are not limited, as long as the capsule core 2 can be made into a whole. The connecting structures 23 comprise but not limited to the following methods:

For example, the connecting structures 23 comprise a fixing member and an adhesive (not shown) connecting the fixing member and the PCB. In a specific embodiment, the connecting structures 23 further comprise a dispensing groove arranged in the fixing member, and the adhesive is used in the dispensing groove to bond the fixing member to the adjacent PCB. In the embodiment in which the fixing member and the adjacent PCB are bonded by the adhesive, the PCB and the fixing member are aligned and then fixed by the adhesive in the dispensing groove, which cannot be repeated below.

Or, for example, the connecting structures 23 comprise a fixing member, a snap hook disposed on one of the fixing element and the PCB, and a snap hook groove on the other. The snap hook and the snap hook groove cooperate to make the fixing member securely connected to the PCB. Generally, the snap hook is disposed on the fixing member, the snap hook groove is cut in the PCB, and the manufacturing process of the PCB is simple.

In addition, the connecting structure 23 has a lead slot (not shown) designed for the flexible circuit board to pass through. Specifically, the lead slot is cut in the fixing member.

Further, the capsule core 2 also comprises a positioning structure 24. The positioning structure 24 comprises a positioning post 241 disposed on one of the connecting structure 23 and the PCB that are adjacent to each other, and a positioning groove 242 in the other for fitting with the positioning post 241. When the two are fixed, the positioning post 241 is inserted into the positioning groove 242, so that the connecting structure 23 and the PCB can remain coaxial, facilitating the arrangement of the antenna unit. Typically, the positioning groove 242 is cut in the PCB, the positioning post 241 is disposed on the connecting structure 23, and the manufacturing process of the PCB is simple.

In a specific embodiment, the positioning post 241 is semi-cylindrical, and the positioning groove 242 is semi-circular. This structure is not limited thereto.

The capsule core 2 of the present application can be described in detail below with specific embodiments.

In the first-type embodiments, the PCB module 21 comprises a first PCB 211 and a second PCB 212 which are arranged along the axial direction of the capsule core 2 and connected by a flexible circuit board. The first PCB 211 has a hollow-out portion 2111.

The functional units 22 comprise a first illuminating unit 221 fixed on the side of the first PCB 211 away from the second PCB 212, and a first photographing unit 222 fixed on the side of the second PCB 212 facing the first PCB 211, wherein at least part of the first photographing unit 222 is located in the hollow-out portion 2111.

Specifically, the first illuminating unit 221 is fixed on the first PCB 211, and the first PCB 211 provides power to the first illuminating unit 221 and controls it to be turned on or off.

The first photographing unit 222 comprises a first camera fixing seat 2221 fixed on the side of the second PCB 212 facing the first PCB 211 and a first camera 2222 fixed on the side of the first camera fixing seat 2221 away from the second PCB 212, wherein the first camera 2222 communicates with the second PCB 212, and the second PCB 212 is used for acquiring and processing images.

The illuminating range of the first illuminating unit 221 partially or completely coincides with the photographing range of the first photographing unit 222. The first illuminating unit 221 illuminates the digestive tract through the end cover 12, which is convenient for the first camera 2222 to capture images through the end cover 12.

The connecting structure 23 comprises a first connecting structure 231 that connects the first PCB 211 and the second PCB 212, wherein the first connecting structure 231 also has a hollow out portion 2315, and the first photographing unit 222 is located in the hollow out portion 2315. Specifically, the first camera 2222 is located in the hollow out portion 2315 so as to capture images through the hollow out portion 2315.

The first connecting structure 231 comprises a holding frame 2311 having a through slot, a first snap hook 2312 disposed on the side of the holding frame 2311 facing the first PCB 211 and a snap hook groove 2313 disposed in the first PCB 211. The first snap hook 2312 engages with the snap hook groove 2313 to fix the first PCB 221 to the first connecting structure 231.

The first connecting structure 231 also comprises a first dispensing groove 2314 disposed on the side of the holding frame 2311 facing the second PCB 212, and a first adhesive (not shown) dispensed in the first dispensing groove 2314 for gluing the first connecting structure 231 to the second PCB 212.

In addition, one of the second PCB 212 and the first connecting structure 231 has a positioning post 241 and the other has a positioning groove 242. When the two are fixed, the positioning post 241 is inserted into the positioning groove 242, so that the two remain coaxial.

Further, the PCB module 21 also comprises a third PCB 213 connected to the side of the second PCB 212 away from the first PCB 211 through the flexible circuit board.

The connecting structures 23 also comprise a second connecting structure 232 connecting the second PCB 212 and the third PCB 213. The second connecting structure 232 comprises a second fixing member 2321 having a holding chamber, a second dispensing groove 2322 on the side of the second fixing member 2321 facing the second PCB 212, a second adhesive in the second dispensing groove 2322 for connecting the second fixing member 2321 to the second PCB 212, a third dispensing groove 2322 on the side of the second fixing member 2321 facing the third PCB 213, and a third adhesive in the third dispensing groove for connecting the second fixing member 2321 to the third PCB 213.

In addition, one of the second PCB 212 and the third connecting structure 233 has a positioning post 241 and the other has a positioning groove 242; when the two are fixed, the positioning post 241 is inserted into the positioning groove 242, so that the two remain coaxial. One of the third PCB 213 and the third connecting structure 233 has a positioning post 241 and the other has a positioning groove 242; when the two are fixed, the positioning post 241 is inserted into the positioning groove 242, so that the two remain coaxial.

Based on the structure of the capsule core with three PCBs, the functional units 22 also comprise a magnet unit and/or a battery unit arranged in the holding chamber. Further, the functional units 22 also comprise an antenna unit welded to the side of the third PCB 213 away from the second PCB 212; or, the functional units 22 also comprise an antenna unit welded to the second PCB 212 and/or the third PCB 213, and the antenna unit is arranged around at least part of the structure of the capsule core.

The magnet unit is used to cooperate with an external processing terminal, and the external processing terminal can apply an external magnetic field to the capsule endoscope 100, and then control the capsule endoscope 100 to do active movement in the digestive tract of a subject via the magnet unit. The battery unit is used to provide power to other functional units.

Or, based on the structure of the capsule core with three PCBs, further, the PCB module 21 also comprises a fourth PCB 214 connected to the side of the third PCB 213 away from the second PCB 212 through the flexible circuit board.

The connecting structures 23 also comprise a third connecting structure 233 connecting the third PCB 213 and the fourth PCB 214. The third connecting structure 233 comprises a third fixing member 2331 connected to the third PCB 213, a fourth dispensing groove in the side of the third fixing member 2331 facing the third PCB 213, a fourth adhesive in the fourth dispensing groove for connecting the third fixing member 2331 to the third PCB 213, a fourth fixing member 2332 connected to the fourth PCB 214, a fifth dispensing groove in the side of the fourth fixing member 2332 facing the fourth PCB 214 and a fifth adhesive in the fifth dispensing groove for connecting the fifth fixing member to the fourth PCB 214.

In addition, one of the third PCB 213 and the third fixing member 2331 has a positioning post 241 and the other has a positioning groove 242; when the two are fixed, the positioning post 241 is inserted into the positioning groove 242, so that the two remain coaxial. One of the fourth PCB 214 and the fourth fixing member 2332 has a positioning post 241 and the other has a positioning groove 242; when the two are fixed, the positioning post 241 is inserted into the positioning groove 242, so that the two remain coaxial.

The functional units 22 also comprise a magnet unit disposed in the holding chamber. The second connecting structure 232 also has the function of fixing the magnet unit. Therefore, those skilled in the art can also call the second connecting structure 232 a magnet fixing member.

The functional units 22 also comprise a battery unit 224 fixed between the third fixing member 2331 and the fourth fixing member 2332. The battery unit 224 comprises a battery assembly 2241 and solder pins 2242 welded to the third PCB 213. The third connecting structure 233 also has the function of fixing the battery unit 224. Therefore, those skilled in the art can also call the third connecting structure 233 a battery fixing member. The battery unit 224 is welded to the third PCB 213 and the fourth PCB 214 to achieve electrical connection, and the PCBs welded to the battery unit 224 is also referred to as a power supply board.

The functional units 22 also comprise an antenna unit 225 welded to the side of the fourth PCB 214 away from the third PCB 213. Or, the functional units 22 also comprise an antenna unit 225 welded to the second PCB 212 and/or fourth PCB 214. The antenna unit 225 comprises solder joints 2251 welded to the second PCB 212 and/or the fourth PCB 214, and an antenna 2252 connected to the solder joints 2251, wherein the antenna 2252 is arranged around at least part of the structure of the capsule core 2 so that the entire capsule core 2 is compact.

The capsule core 2 in all of the above embodiments is generally assembled in an enclosure 1 with a transparent end cover 12, and the first photographing unit 222 and the first illuminating unit 221 are located at the end cover 12.

In addition, the first connecting structure 231 also has a protrusion 2316 protruding outward for inserting into the fixing groove of the enclosure 1, so that the entire capsule core 2 can be fixed to the enclosure 1.

In the second-type embodiments, the capsule core 2 has two photographing units.

In a specific embodiment, referring to FIGS. 6-10, on the basis of the embodiment where the fourth PCB 214 is provided, the antenna unit 225 is welded to the second PCB 212 and/or the fifth PCB 215, and the antenna unit 215 is arranged around at least part of the structure of the capsule core 2. The PCB module 21 further comprises an annular fifth PCB 215 connected to the side of the fourth PCB 214 away from the third PCB 213 through the flexible circuit board, and the fifth PCB 215 has a second hollow out portion.

The functional units 22 comprise a second illuminating unit 226 fixed on the side of the fifth PCB 215 away from the fourth PCB 214, and a second photographing unit 227 fixed on the side of the fourth PCB 214 facing the fifth PCB 215, wherein at least part of the second photographing unit 227 is located in the second hollow out portion.

The connecting structures 23 also comprise a fourth connecting structure 234 connecting the fourth PCB 214 and the fifth PCB 215. The fourth connecting structure 234 comprises a holding frame with a through slot, a second snap hook disposed on the side of the holding frame facing the fifth PCB 215, a second snap hook groove disposed in the fifth PCB 215, a sixth dispensing groove in the side of the holding frame 2311 facing the fourth PCB 214, and a sixth adhesive in the sixth dispensing groove for connecting the fourth connecting structure 234 and the fourth PCB 214.

Specifically, the fourth connecting structure 234 and the first connecting structure 231 are the same and arranged symmetrically, the second illuminating unit 226 and the first illuminating unit 221 are the same and arranged symmetrically, and the second photographing unit 227 and the first photographing unit 222 are the same and arranged symmetrically.

Or, in an another embodiment (not shown), on the basis of the embodiment where the PCB module 21 comprises a first PCB, a second PCB and a third PCB, the antenna unit is welded to the second PCB or the third PCB, and the antenna unit is arranged around at least part of the structure of the capsule core, the PCB module 21 further comprises an annular sixth PCB connected to the side of the third PCB away from the second PCB through the flexible circuit board, and the sixth PCB has a third hollow out portion.

The functional units comprise a second illuminating unit fixed on the side of the sixth PCB away from the third PCB, and a second photographing unit fixed on the side of the third PCB facing the sixth PCB, wherein at least part of the second photographing unit is located in the third hollow out portion.

The connecting structures also comprise a fifth connecting structure connecting the third PCB and the sixth PCB. The fifth connecting structure comprises a holding frame with a through slot, a third snap hook disposed on the side of the holding frame facing the sixth PCB, a third snap hook groove disposed in the sixth PCB, a seventh dispensing groove in the side of the holding frame facing the third PCB, and a seventh adhesive in the seventh dispensing groove for connecting the fifth connecting structure and the third PCB.

Specifically, the fifth connecting structure and the first connecting structure are the same and arranged symmetrically, the second illuminating unit and the first illuminating unit are the same and arranged symmetrically, and the second photographing unit and the first photographing unit are the same and arranged symmetrically.

The capsule core 2 in the second-type embodiments is generally assembled in an enclosure 1 with two transparent end covers 12. The first photographing unit 222 and the first illuminating unit 221 are located at one end cover 12, and the second photographing unit 222 and the second illuminating unit 221 are located at another end cover 12.

In addition, the capsule core 2 and the enclosure 1 in the embodiments can be fixed using, but not limited to, the following methods: the first connecting structure 231 is not provided with the protrusion 2316, and one end of the main enclosure 11 is provided with an inwardly protruding snap-fit protrusion 113; inserting the capsule core 2 that is assembled into a whole by the connecting structures 23 from the top of the main enclosure 11, at this point, the snap-fit protrusion 113 bears against a part of the structure of the capsule core 2; then, dispensing adhesive at the positions on the other end of the main enclosure 11 corresponding to the capsule core 2. Specifically, the snap-fit protrusion bears against the first connecting structure 231, and the fourth connecting structure 234 is fixed to the other end of the main enclosure 11 by dispensing adhesive.

In summary, the capsule core 2 disclosed in the embodiments comprises connecting structures 23 for connecting adjacent PCBs, and the functional units 22 are mounted on the PCBs or the connecting structures 23, so that the capsule core 2 forms a whole structure, which is convenient for fixing to the enclosure 1.

It should be understood that, although the specification is described in terms of embodiments, not every embodiment merely comprises an independent technical solution. Those skilled in the art should have the specification as a whole, and the technical solutions in each embodiment may also be combined as appropriate to form other embodiments that can be understood by those skilled in the art.

The series of detailed descriptions listed above are only specific descriptions of the feasible embodiments of the present invention, and are not intended to limit the protection scope of the present invention. Any equivalent embodiments or variations made without departing from the technical spirit of the present invention should be included in the protection scope of the present invention.

What is claimed is:

1. A capsule core, comprising:
   a printed circuit board module, comprising a plurality of printed circuit boards connected through flexible circuit boards and spaced apart;
   a plurality of connecting structures for connecting adjacent printed circuit boards; and
   a plurality of functional units that are mounted on the printed circuit boards or the connecting structures, at least part of the functional units communicating with the printed circuit boards;
   wherein the printed circuit board module comprises a first printed circuit board and a second printed circuit board which are arranged along the axial direction of the capsule core and connected by a flexible circuit board, the first printed circuit board comprises a hollow-out portion;

the functional units comprise a first illuminating unit fixed on the side of the first printed circuit board away from the second printed circuit board, and a first photographing unit fixed on the side of the second printed circuit board facing the first printed circuit board, wherein at least part of the first photographing unit is located in the hollow-out portion;

the connecting structures comprise a first connecting structure connecting the first printed circuit board and the second printed circuit board, the first connecting structure comprising a holding frame with a through slot, a first snap hook disposed on the side of the holding frame facing the first printed circuit board, a first snap hook groove disposed in the first printed circuit board, a first dispensing groove in the side of the holding frame facing the second printed circuit board, and a first adhesive in the first dispensing groove for connecting the first connecting structure and the second printed circuit board.

2. The capsule core of claim 1, wherein the connecting structures comprise a lead slot for the flexible circuit boards to pass through.

3. The capsule core of claim 1, wherein the capsule core further comprises a positioning structure, wherein the positioning structure comprising a positioning post disposed on one of the connecting structure and the printed circuit board that are adjacent to each other, and a positioning groove in the other of the connecting structure and the printed circuit board for fitting with the positioning post.

4. The capsule core of claim 1, wherein the printed circuit board module further comprises a third printed circuit board connected to the side of the second printed circuit board away from the first printed circuit board through a flexible circuit board, and a fourth printed circuit board connected to the side of the third printed circuit board away from the second printed circuit board through a flexible circuit board;

the connecting structures further comprise a second connecting structure connecting the second printed circuit board and the third printed circuit board, the second connecting structure comprising a second fixing member having a holding chamber, a second dispensing groove in the side of the second fixing member facing the second printed circuit board, a second adhesive in the second dispensing groove for connecting the second fixing member to the second printed circuit board, a third dispensing groove in the side of the second fixing member facing the third printed circuit board, and a third adhesive in the third dispensing groove for connecting the second fixing member to the third printed circuit board; and the connecting structures further comprise a third connecting structure connecting the third printed circuit board and the fourth printed circuit board, the third connecting structure comprising a third fixing member connected to the third printed circuit board, a fourth dispensing groove in the side of the third fixing member facing the third printed circuit board, a fourth adhesive in the fourth dispensing groove for connecting the third fixing member to the third printed circuit board, a fourth fixing member connected to the fourth printed circuit board, a fifth dispensing groove in the side of the fourth fixing member facing the fourth printed circuit board and a fifth adhesive in the fifth dispensing groove for connecting the fifth fixing member to the fourth printed circuit board;

the functional units further comprise a magnet unit arranged in the holding chamber;

the functional units further comprise a battery unit, wherein the battery unit is fixed on at least one of the third fixing member and the fourth fixing member, and is located between the third fixing member and the fourth fixing member, and the battery unit is welded to the third printed circuit board and the fourth printed circuit board; and the functional units further comprise an antenna unit welded to the side of the third printed circuit board away from the second printed circuit board or, the functional units further comprise an antenna unit welded to the second printed circuit board and/or the third printed circuit board, wherein the antenna unit is arranged around at least part of the structure of the capsule core.

5. The capsule core of claim 4, wherein the printed circuit board module further comprises an annular fifth printed circuit board connected to the side of the fourth printed circuit board away from the third printed circuit board through a flexible circuit board, the fifth printed circuit board comprises a second hollow out portion;

the functional units comprise a second illuminating unit fixed on the side of the fifth printed circuit board away from the fourth printed circuit board, and a second photographing unit fixed on the side of the fourth printed circuit board facing the fifth printed circuit board, wherein at least part of the second photographing unit is located in the second hollow out portion;

the connecting structures further comprise a fourth connecting structure connecting the fourth printed circuit board and the fifth printed circuit board, the fourth connecting structure comprising a holding frame with a through slot, a second snap hook disposed on the side of the holding frame facing the fifth printed circuit board, a second snap hook groove disposed in the fifth printed circuit board, a sixth dispensing groove in the side of the holding frame facing the fourth printed circuit board, and a sixth adhesive in the sixth dispensing groove for connecting the fourth connecting structure and the fourth printed circuit board;

the antenna unit is welded to the second printed circuit board and/or the fourth printed circuit board, and the antenna unit is arranged around at least part of the structure of the capsule core.

6. The capsule core of claim 4 is part of a capsule endoscope, comprising an enclosure.

7. The capsule core of claim 1, wherein the printed circuit board module further comprises a third printed circuit board connected to the side of the second printed circuit board away from the first printed circuit board through a flexible circuit board;

the connecting structures further comprise a second connecting structure connecting the second printed circuit board and the third printed circuit board, the second connecting structure comprising a second fixing member having a holding chamber, a second dispensing groove in the side of the second fixing member facing the second printed circuit board, a second adhesive in the second dispensing groove for connecting the second fixing member to the second printed circuit board, a third dispensing groove in the side of the second fixing member facing the third printed circuit board, and a third adhesive in the third dispensing groove for connecting the second fixing member to the third printed circuit board;

the functional units further comprise a magnet unit and/or a battery unit arranged in the holding chamber.

8. The capsule core of claim 7, wherein the functional units further comprise an antenna unit welded to the side of the third printed circuit board away from the second printed circuit board;

or, the functional units further comprise an antenna unit welded to the second printed circuit board and/or the third printed circuit board, the antenna unit is arranged around at least part of the structure of the capsule core.

9. The capsule core of claim 7, wherein the printed circuit board module further comprises an annular sixth printed circuit board connected to the side of the third printed circuit board away from the second printed circuit board through a flexible circuit board, the sixth printed circuit board comprises a third hollow out portion;

the connecting structures further comprise a fifth connecting structure connecting the third printed circuit board and the sixth printed circuit board, the fifth connecting structure comprising a holding frame with a through slot, a third snap hook disposed on the side of the holding frame facing the sixth printed circuit board, a third snap hook groove disposed in the sixth printed circuit board, a seventh dispensing groove in the side of the holding frame facing the third printed circuit board, and a seventh adhesive in the seventh dispensing groove for connecting the fifth connecting structure and the third printed circuit board;

the functional units further comprise an antenna unit welded to the second printed circuit board and/or the third printed circuit board, the antenna unit is arranged around at least part of the structure of the capsule core;

the functional units comprise a third illuminating unit fixed on the side of the sixth printed circuit board away from the third printed circuit board, and a third photographing unit fixed on the side of the third printed circuit board facing the sixth printed circuit board, wherein at least part of the third photographing unit is located in the third hollow out portion.

\* \* \* \* \*